(12) United States Patent
Wagner et al.

(10) Patent No.: US 11,340,209 B2
(45) Date of Patent: May 24, 2022

(54) MEASURING HUMIDITY OR MOISTURE WITH SENSOR DRIFT COMPENSATION

(71) Applicant: Wagner Electronic Products, Inc., Rogue River, OR (US)

(72) Inventors: Edward D. Wagner, Rogue River, OR (US); Timothy Duncan, Grants Pass, OR (US); Anis Messaoud, Rogue River, OR (US)

(73) Assignee: Wagner Electronic Products, Inc., Rogue River, OR (US)

( * ) Notice: Subject to any disclaimer, the term of this patent is extended or adjusted under 35 U.S.C. 154(b) by 156 days.

(21) Appl. No.: 16/824,361

(22) Filed: Mar. 19, 2020

(65) Prior Publication Data

US 2020/0300833 A1    Sep. 24, 2020

Related U.S. Application Data

(60) Provisional application No. 62/822,773, filed on Mar. 22, 2019.

(51) Int. Cl.
| | | |
|---|---|---|
| *G01N 33/38* | (2006.01) | |
| *G01N 27/00* | (2006.01) | |
| *G01K 13/00* | (2021.01) | |
| *G01K 7/01* | (2006.01) | |
| *G01N 27/22* | (2006.01) | |
| *G01N 27/12* | (2006.01) | |
| *G01N 27/60* | (2006.01) | |

(52) U.S. Cl.
CPC ............. *G01N 33/383* (2013.01); *G01K 7/01* (2013.01); *G01K 13/00* (2013.01); *G01N 27/223* (2013.01); *G01N 27/121* (2013.01); *G01N 27/605* (2013.01)

(58) Field of Classification Search
CPC ............... G01N 33/383; G01N 27/121; G01N 27/223; G01N 27/605
See application file for complete search history.

(56) References Cited

U.S. PATENT DOCUMENTS

| 2,665,409 A * | 1/1954 | Rogers ................. G01N 27/223 |
| | | 324/670 |
| 4,272,718 A * | 6/1981 | Kashiuchi .......... G01R 27/2605 |
| | | 324/601 |
| 2004/0012912 A1 * | 1/2004 | Rombach ............... G01N 25/56 |
| | | 361/321.6 |

(Continued)

*Primary Examiner* — Herbert K Roberts
(74) *Attorney, Agent, or Firm* — Klarquist Sparkman, LLP

(57) ABSTRACT

Sensor accuracy issues may arise when a humidity sensor is kept in a high humidity environment for an extended period of time. In these circumstances, a humidity sensor reading may tend to may become less accurate over time. To improve the accuracy of sensor readings, methods and systems described herein estimate and correct for sensor drift in high humidity conditions. Methods and systems described herein may use memory to store past humidity or other sensor readings so that an estimated amount of sensor drift may be determined to improve the accuracy of sensor readings. A memory may be embedded in a sensor module so that past readings for a given sensor module are stored in the memory of the sensor module. Algorithms for sensor drift compensation, and systems and methods that use such algorithms to improve the accuracy of sensor readings, are disclosed herein.

16 Claims, 10 Drawing Sheets

(56) References Cited

U.S. PATENT DOCUMENTS

| | | | |
|---|---|---|---|
| 2005/0253912 A1* | 11/2005 | Smith | B41J 2/04586 |
| | | | 347/102 |
| 2014/0032153 A1* | 1/2014 | Mayer | G01N 33/0006 |
| | | | 702/104 |
| 2014/0278186 A1* | 9/2014 | Herzl | G01N 33/0006 |
| | | | 702/104 |
| 2017/0038327 A1* | 2/2017 | Ledwosinska | G01N 27/225 |
| 2017/0138881 A1* | 5/2017 | Krapf | G01N 33/383 |
| 2019/0195820 A1* | 6/2019 | Fornasari | G01N 33/18 |
| 2019/0339224 A1* | 11/2019 | Bhavaraju | A61B 5/14532 |

* cited by examiner

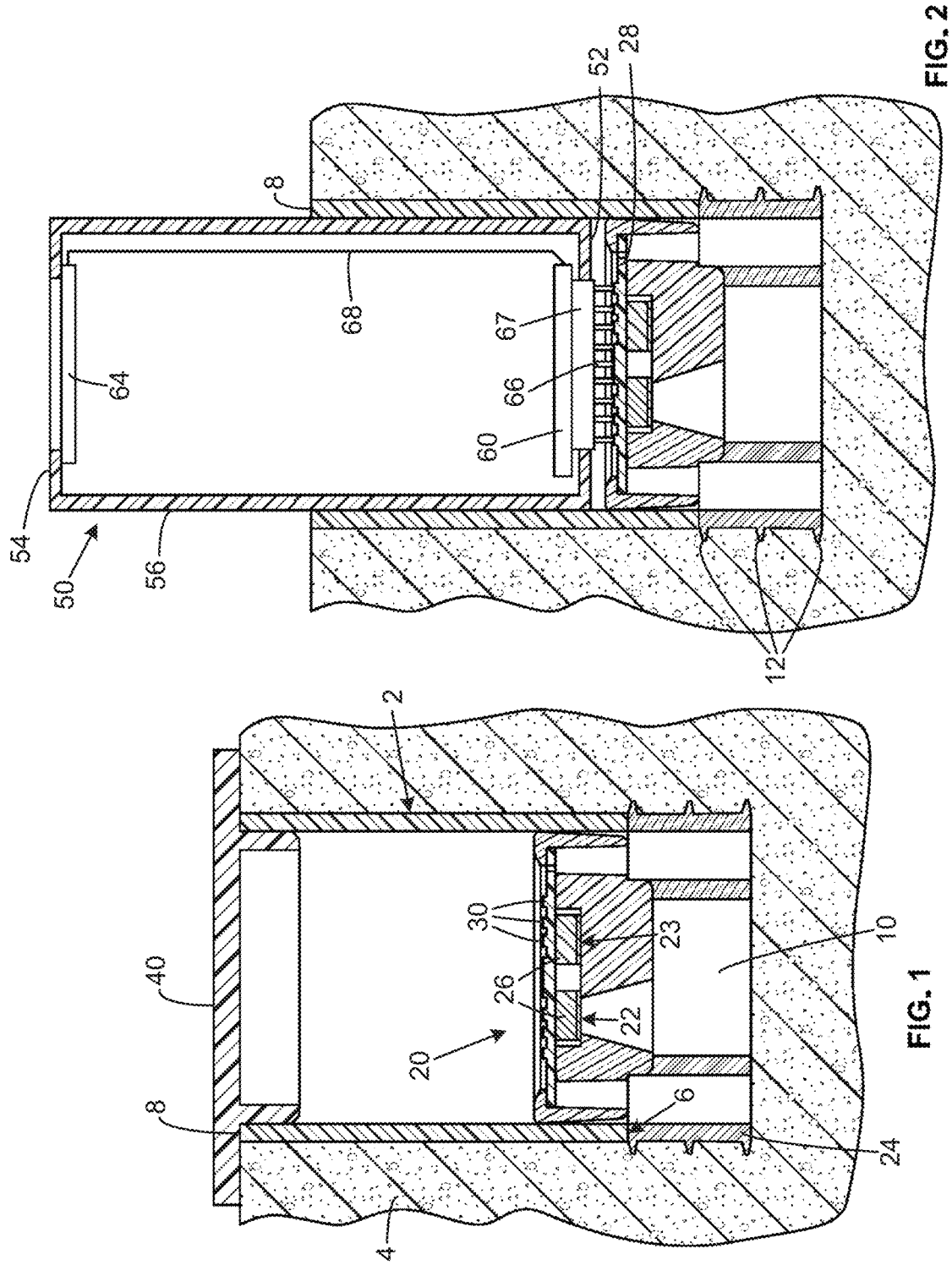

MEASURING HUMIDITY OR MOISTURE WITH SENSOR DRIFT COMPENSATION

CROSS REFERENCE TO RELATED APPLICATION

This application claims priority from U.S. Provisional Application No. 62/822,773, filed Mar. 22, 2019, which application is incorporated herein by reference in its entirety.

BACKGROUND

Relative humidity (RH) within concrete can be measured by performing in-situ testing at different depths within a concrete slab. An RH gradient exists within a slab of concrete that has its outer surface exposed; the RH increases as the depth into the slab increases. When the outer surface of the concrete slab is covered by a material that is close to impermeable, thereby preventing moisture from migrating out of the concrete surface, the RH gradient equalizes to an average RH throughout the slab that is about equal to the RH at 40% depth of an uncovered slab drying from the surface only (resting on a vapor retarder), or equal to the RH at 20% depth of an uncovered slab drying from both top and bottom.

A conventional practice for measuring RH in concrete includes forming a hole into a concrete slab at a certain depth, inserting a liner into the hole that will allow for sealing off the sidewalls of the concrete, placing of a seal at the top of the liner to seal off the internal environment, allowing for the equilibration of the RH of the internal environment, and then inserting a testing instrument into the liner to measure the RH. Most currently available instruments consist of a hole liner into which is inserted a probe that includes the sensor and a plastic enclosure. The probe is allowed to equilibrate, then taken out and moved to the next sleeve for the next measurement.

However, these currently available instruments result in undesirable problems relating to the thermal equilibrium of the sensing device and the concrete. Because RH is temperature dependent, an RH sensing element should be in thermal equilibrium with the environment being measured. With these currently available instruments, the probe portion that is inserted into the hole liner needs to come to thermal equilibrium with the concrete before an accurate measurement can be made. When a person handles the probe before insertion, heat is transferred into the probe, making the probe warmer and making the RH readings less accurate. Also, the ambient air is often times at a different temperature than the concrete environment to be measured, causing heat transfer across the probe. Even 1° F. of temperature change in the sensing element can cause inaccuracies in RH measurement of several percent.

SUMMARY

Disclosed herein are exemplary apparatuses and methods that make measuring humidity or moisture in a subject material, such as a concrete slab, quicker, simpler and more accurate, among other benefits.

In one aspect, an apparatus for measuring humidity, moisture, and/or temperature in a material such as concrete, includes a sensor module and, in some cases, a reader module. The sensor module can be mounted within a sleeve that is embedded in the subject material and the reader module can be inserted into the sleeve to connect with the sensor module in order to take a reading. The sensor module can remain embedded in the material, thus allowing a sensor of the sensor module to remain in thermal equilibrium. The hand-held reader module can be connected to various sensor modules to receive humidity, moisture, and/or temperature readings corresponding to various locations within one or more concrete slabs or other materials. Thus, because each sensor module is already in thermal equilibrium, measurement speed is improved.

The sensor module includes a humidity or moisture sensor electrically connected to a first electrical connector. The reader module includes a second electrical connector that is mateable with the first electrical connector to establish an electrical connection between the sensor module and the reader module. The reader module is electrically connectable to and electrically disconnectable from the sensor module. The second electrical connector is electrically connectable to the first electrical connector regardless of a rotational orientation of the reader module relative to the sensor module. One of the electrical connectors can be a set of spring-loaded connector pins while the other electrical connector can be a set of coplanar, concentric landing pads, such as on a printer circuit board, such that redundant pairs of the pins are arranged to contact the same landing pad when the reader module is connected to the sensor module.

Using separate sensor modules allows each RH reading to be more accurate because heat transfer disruptions at the sensor are minimized. Heat transfer can be minimized due to a combination of various advantageous factors, such as: (1) the sensor module remains within the subject material so that the sensor is at thermal equilibrium with the subject material when the sleeve cover is removed; (2) the use of polymer materials for the sleeve and housings that have low thermal conductivity; (3) the minimized contact area between connector pins of the reader module and landing pads of the sensor module; (4) the rotation non-specific nature of the electrical connection between the reader and sensor modules; and (5) the automatic touch-and-sense feature, which results in a minimized time delay between inserting the reader module and the measurements being taken. Each of these benefits is described in detail below.

However, accuracy issues may arise when a sensor module is kept in a high humidity environment for an extended period of time. A humidity sensor may tend to drift such that a humidity reading becomes less accurate over time in relatively humid conditions. FIG. 12 illustrates an example of this sensor drift. As shown at FIG. 12, a relative humidity (RH) reading (labeled "Sensor RH") may tend to drift apart from a true relative humidity (labeled "Reference RH") as time progresses, with the error increasing as time goes in. Moreover, the error may be more than a few percent.

To improve the accuracy of sensor readings, methods and systems described herein estimate and correct for sensor drift in high humidity conditions. Accordingly, methods and systems described herein may use memory to store past humidity or other sensor readings so that an estimated amount of sensor drift may be determined to improve the accuracy of sensor readings. A memory may be embedded in each sensor module so that past readings for a given sensor module are stored in the memory of the sensor module. Accordingly, algorithms for sensor drift compensation, and systems and methods that use such algorithms to improve the accuracy of sensor readings, are disclosed herein.

Additionally, the use of past sensor readings to compensate for drift incentivizes the regular taking of and storage of sensor readings. Thus, in some embodiments, sensor modules may be provided with on-board controllers and power sources that enable a sensor module to regularly wake itself, take sensor readings, and store the sensor readings in memory even without connection to an external power source (e.g., without connection to a reader module). Thus, even if sensor readings are not regularly captured using a reader module, a sensor module may obtain a stored history of sensor readings that may be used to compensate for drift correction.

Additionally, in some embodiments, sensor modules may be provided with wireless transceivers that may be used to wirelessly communicate with other sensor modules (e.g., via mesh networks or other types of networks) or other computing devices (e.g., servers, reader modules, and the like), which may enable sensor readings to be automatically collected and analyzed without use of a reader module.

The foregoing and other objects, features, and advantages of the invention will become more apparent from the following detailed description, which proceeds with reference to the accompanying figures.

BRIEF DESCRIPTION OF THE DRAWINGS

FIG. 1 is a cross-sectional view of an exemplary sleeve embedded in a material and having an exemplary sensor module mounted within the sleeve and a cover mounted over the sleeve.

FIG. 2 is a cross-sectional view of the sleeve and sensor module of FIG. 1, wherein the cover is removed and an exemplary reader module is inserted within the sleeve and is in electrical contact with the sensor module.

DETAILED DESCRIPTION

Figure 3:
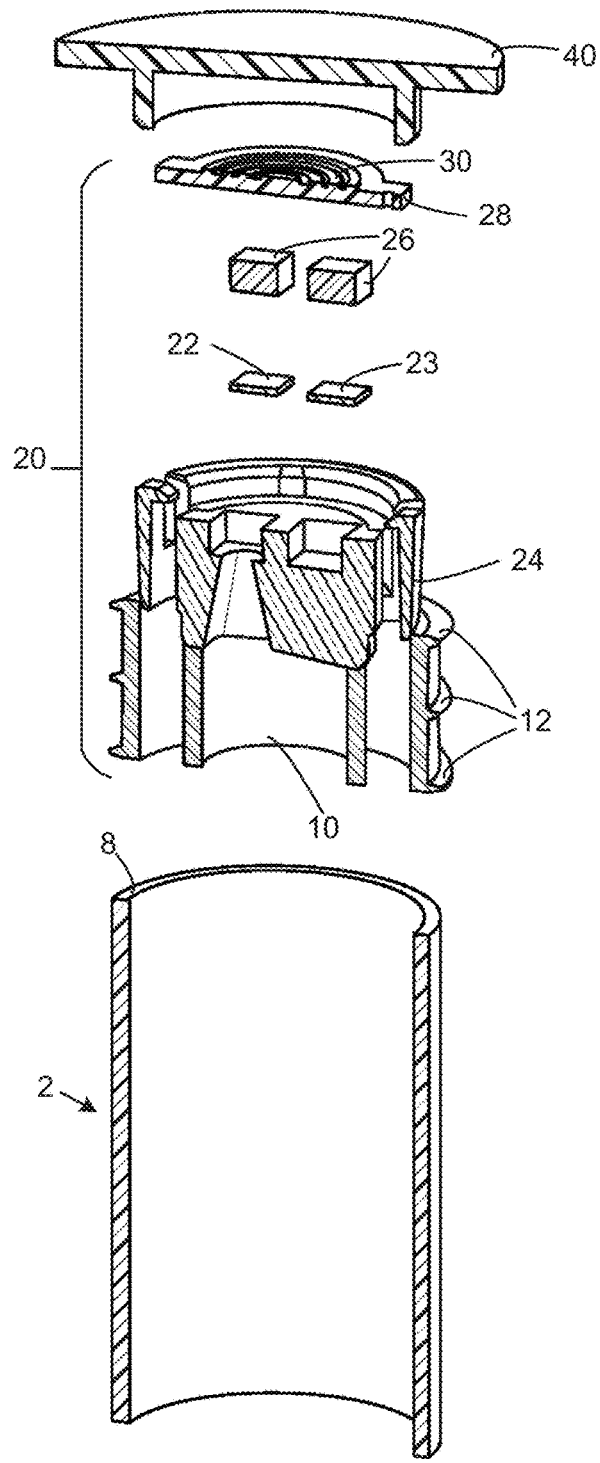
FIG. 3 is an exploded cross-sectional perspective view of the sleeve, sensor module and cover of FIG. 1.

Described herein are exemplary embodiments of devices and related methods for measuring humidity or moisture. The following description is exemplary in nature and is not intended to limit the scope, applicability, or configuration of the invention in any way. Various changes to the described embodiments and methods may be made in the function and arrangement of the elements described herein without departing from the scope of the invention.

As used in this application, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed methods may be described in a particular, sequential order for convenient presentation, it should be understood that certain of the disclosed embodiments can encompass an order of operations other than the particular, sequential order disclosed. For example, operations described sequentially may in some embodiments be rearranged or performed concurrently. Further, descriptions and disclosures provided in association with one particular embodiment are not limited to that embodiment, and may be applied to other embodiments disclosed.

Embodiments described herein include features that enable humidity or moisture measurement, such as relative humidity (RH) measurement, in a subject material, such as concrete, without the disturbing effects of heat transfer from a user, ambient air, and/or the probe itself to the sensor, resulting in more accurate measurements. Exemplary subject materials can include water containing construction materials, such as concrete, cement, gypsum, wood and wood-based materials, and any other material having humidity, moisture, and/or other water content. While exemplary embodiments are shown in the accompanying figures and related descriptions that relate to measuring RH in concrete, it should be understood that these embodiment can be used with various subject materials other than or in addition to concrete, and that alternative embodiments can be configured to measure other characteristics of the subject material other than or in addition to RH, such as temperature and light sensitivity.

FIG. 1 shows a sleeve 2 and housing 24 that are embedded into a hole in a portion of a subject material 4, such as concrete. The concrete hole can be formed by conventional means, such as drilling or pushing the sleeve 2 and/or housing 24 into wet concrete. The sleeve 2 can comprise a tube, such as a generally right-cylindrical tube, having a lower end 6 abutting a housing 24 within the concrete and an open upper end 8 at the surface of the concrete. The housing 24 can comprise an opening 10 that exposes a portion of the concrete 4 below the sleeve 2 and housing 24 to a hollow lumen within the housing 24. The sleeve 2 and/or housing 24 can also comprise one or more ribs or other irregular features 12 on its outer side surface that engage with the surrounding concrete 4. The ribs 12 can isolate and maintain an equilibrium environment of the effused moisture vapor underneath the sleeve 2 and/or housing 24 as well as resist movement of the sleeve with respect to the concrete.

A sensor module 20 can be insertable into and removable from the sleeve 2. The sensor module 20 is shown in FIGS. 1 and 2 in a functional position abutting the lower end 6 of the sleeve 2, making a compression fit that acts to seal off the environment underneath that is to be measured. The sensor module 20 can comprise one or more sensor submodules 22 for measuring the absolute humidity and/or temperature of the adjacent concrete that is exposed via the lower opening 10 of the sleeve 2, one or more memory submodules 23 for storing readings taken by the one or more sensor submodules 22, and/or other submodules. For example, although not shown in FIGS. 1-4, additional submodules of the sensor module 20 may include a controller submodule 25 and/or a transceiver submodule 27.

Figure 4:
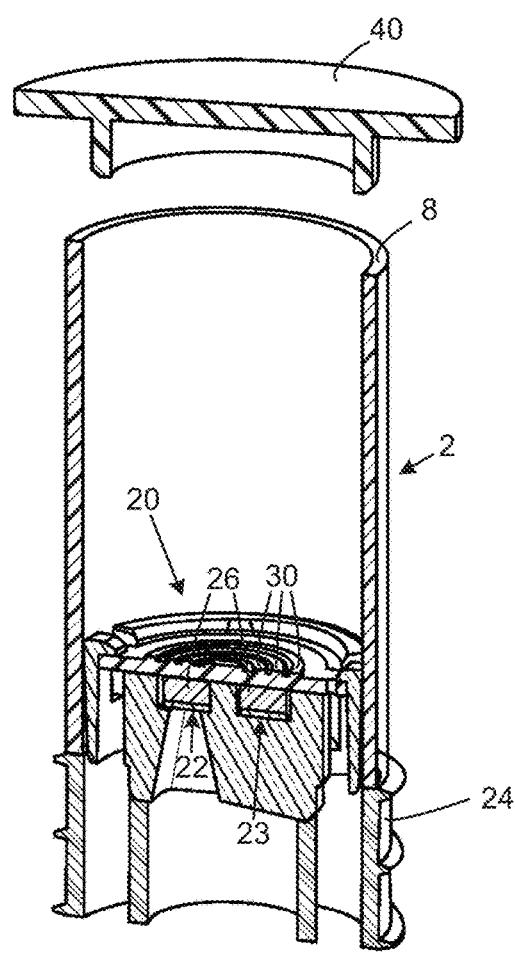
FIG. 4 is cross-sectional perspective view showing the sleeve, sensor module and cover of FIG. 1 assembled together.

As shown in FIGS. 3 and 4, the sensor module 20 can comprises the housing 24, one or more zebra strips or other equivalent electrical connector 26, and a set of electrical connection terminals, such as a printed circuit board (PCB) 28 comprising a plurality of concentric landing pads 30. The sensor submodule 22 and/or memory submodule 23 (as well as other submodules if present) can be electrically coupled to the PCB 28 via zebra strips 26. The sleeve 2 and the housing 24 can be comprised of polymeric material selected to have low thermal conductivity in order to reduce heat transfer to the sensor submodule 22, with exemplary materials including acrylonitrile butadiene styrene (ABS) and high impact polystyrene (HIPS).

Figure 6:
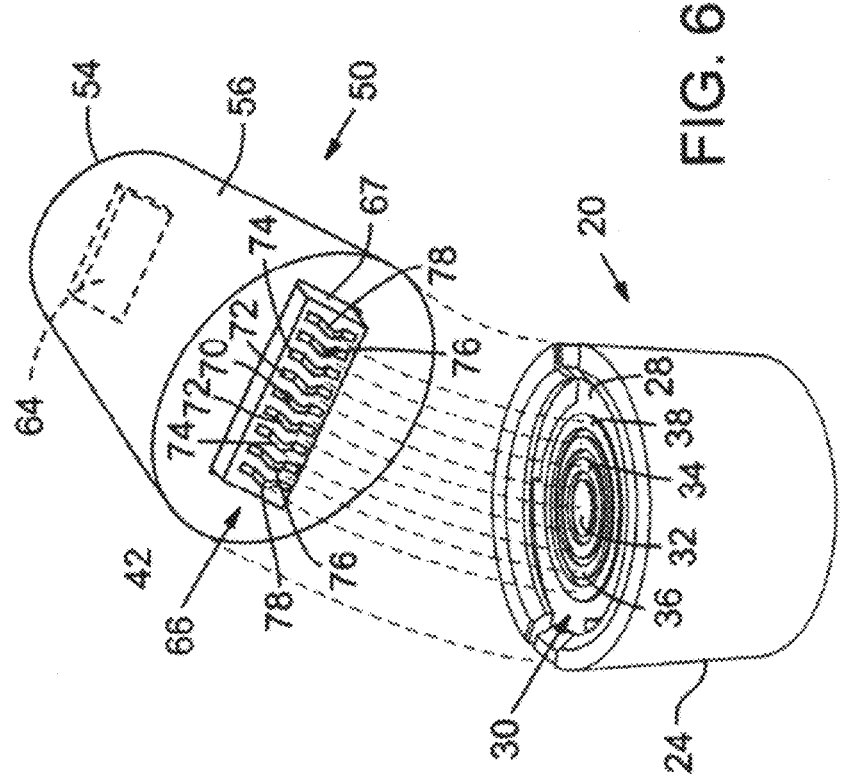
FIG. 6 is a perspective view of the sensor module and reader module of FIG. 2, showing how an electrical connection is made between a set of connector pins on the reader module and a set of concentric landing pads on the sensor module.

As shown in FIG. 6, the landing pads 30 can comprise a disk-shaped central pad 32 and one or more annular rings, such as first ring 34, a second ring 36, and a third ring 38. The landing pads 30 can comprise electrically conductive material, such as gold-plated copper traces, and can be separated from one another by rings of insulating material, such a fiberglass or silicon-based material. Each of the landing pads 30 can comprise a planar upper contact surface and all of the planar upper contact surfaces can be coplanar. This geometry can be established by the use of the PCB 28, which fixes the relative positions of the landing pads 30. The PCB 28, being composed primarily of material having low thermal conductivity, can further help reduce heat transfer to the sensor submodule 22.

The lower opening 10 of the housing 24 can be covered with a water-permeable material, such as Gortex®, that can prevent debris from entering the sleeve and interfering with the sensor submodule 22, while allowing water vapor to pass. Such a cover material can be used, for example, when the sleeve 2 is to be inserted into wet concrete that could otherwise seep into the sleeve via the lower opening 10.

The open upper end 8 of the sleeve 2 can be enclosed with a cover 40, as shown in FIG. 1. The cover 40 can seal off the inner lumen of the sleeve 2 and protect the sensor module 20 exposure to the external atmosphere and reduce heat transfer between the ambient air and the sensor module 20. The cover 40 can be removed temporarily when an RH reading is to be taken from the sensor submodule 22.

With the cover 40 removed, a reader module 50 can be inserted into the sleeve 2, as shown in FIG. 2, in order to perform an RH measurement. The reader module 50 can be configured such that an RH measurement is performed automatically in response to the reader module making contact with the sensor module 20 within the sleeve 2. In the embodiment shown, the reader module 50 comprises an elongated cylindrical housing having a lower end 52, an upper end 54, and a side wall 56. The configuration of the side wall 56 can be selected such that the lower end 52 of the reader module 50 fits closely within the inner lumen of the sleeve 2.

In an exemplary method of use, the sensor module 20 is left within the sleeve 2 with the cover 40 in place such that a thermal equilibrium is maintained between the sensor module 20, the sleeve 2, and the concrete 4. When an RH measurement is to be taken, a user can remove the cover 40 and insert the reader module 50 into the sleeve 2 until the lower end 52 contacts the sensor module 20. The reader module 50 can then automatically and quickly take absolute humidity and temperature readings from the sensor module 20 before any significant amount of heat is transferred from the reader module and/or the ambient air to the sensor module.

Figure 5:
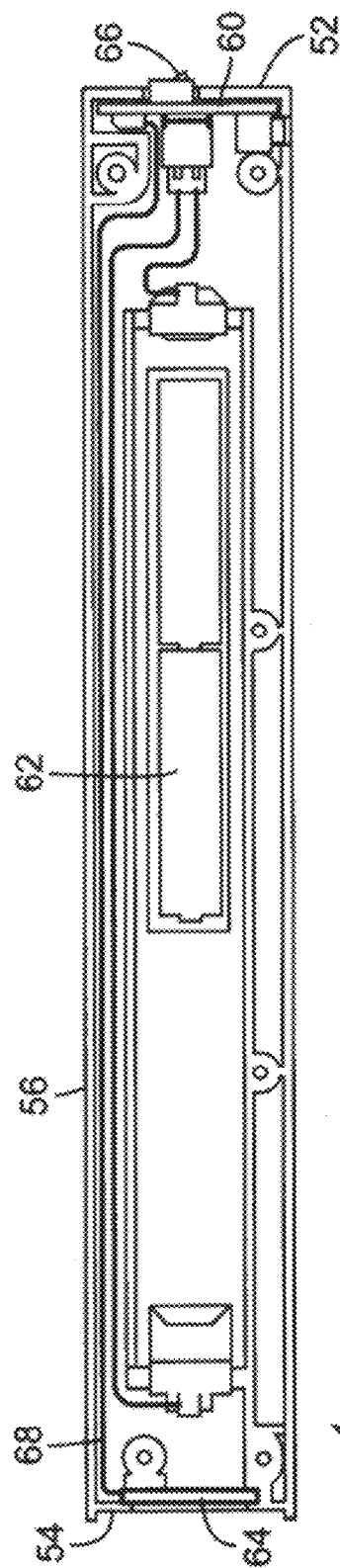
FIG. 5 is a plan view of the reader module of FIG. 2 with part of its housing removed.

As shown in FIG. 5, the reader module 50 can comprise a controller 60 electrically coupled to a power source 62, a display 64, and a plurality of electrical terminals 66. The controller 60 can comprise a microcontroller and/or microprocessor configured to interact with the sensor submodule 22 and the display 64, as described below. The power source 62 can comprise one or more batteries, for example, positioned within the reader housing. The display 64 can be positioned at the upper end 54 of the housing and can comprise a liquid crystal display (LCD), for example. The display 64 can be electrically coupled to the controller 60 via an electrical interconnect 68. In some embodiments, the reader module 50 may further comprise a transceiver 65 (not shown in FIGS. 5-6), which may be a separate component from controller 60 or part of controller 60.

Figure 7A:
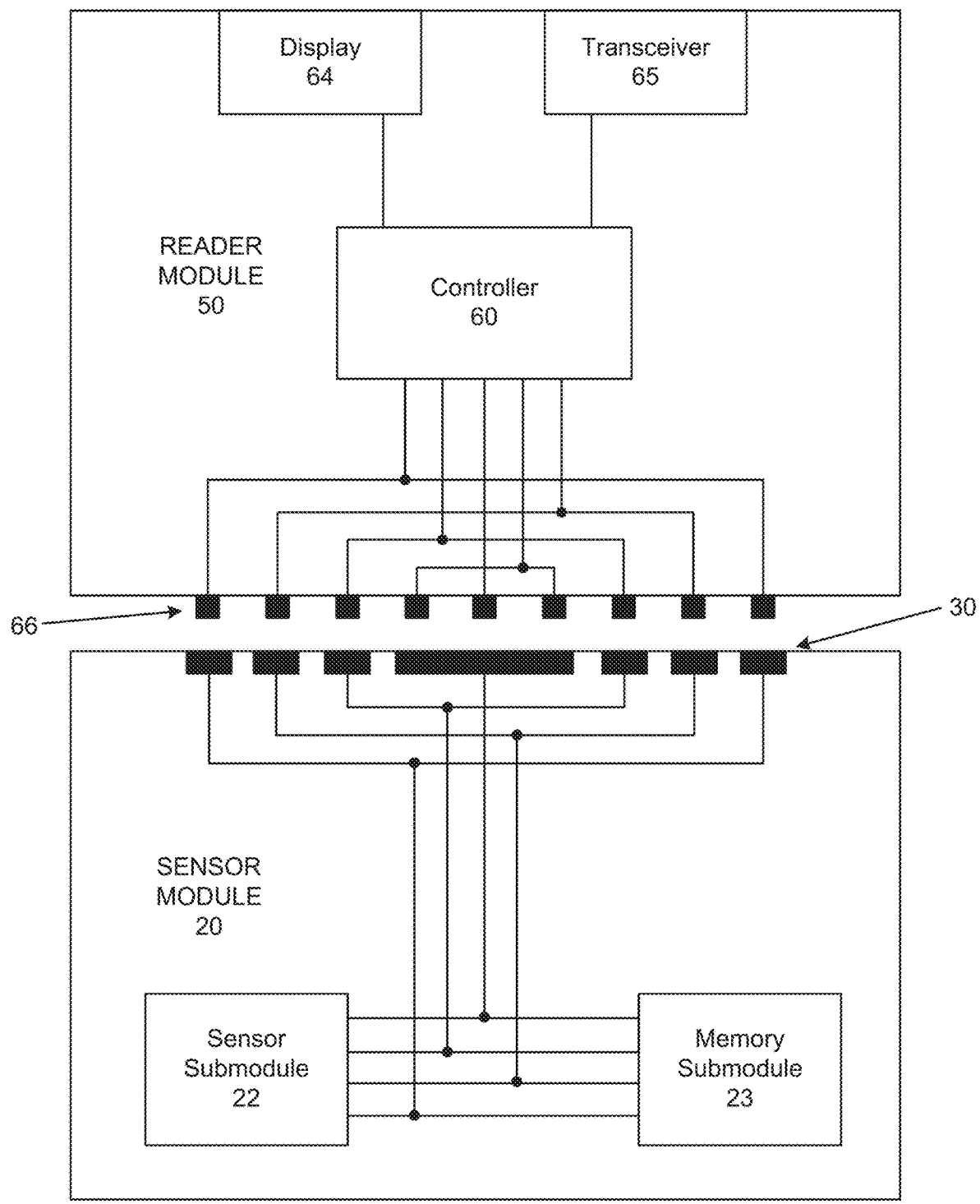
FIG. 7A is a schematic diagram showing elements of and electrical connections between an exemplary reader module and sensor module.

As shown in FIG. 6, the plurality of electrical terminals 66 can be a plurality of connector pins, which can include a center pin 70 and one or more redundant pin pairs, such as a first pin pair 72, a second pin pair 74, a third pin pair 76 and a fourth pin pair 78. As shown in FIG. 7A, each pair of redundant pins can be directly connected together and electrically coupled to a single line of the controller 60. As shown in FIG. 6, the plurality of connector pins 66 can included in a single board-to-board connector component 67 having spring loaded contacts and that is coupled to the controller 60.

When the reader module 50 is inserted within the sleeve 2, the pins 66 contact the landing pads 30 to electrically connect the controller 60 with the sensor submodule 22. As shown in FIGS. 6 and 7A, the center pin 70 and the first pin pair 72 contacts the central pad 32, the second pin pair 74 contacts the first ring 34, the third pin pair 76 contacts the second ring 36, and the fourth pin pair 78 contacts the third ring 38. As shown in FIG. 2, the contact between the pins 66 and the pads 30 can be the sole contact between the reader module 50 and sensor module 20. This pin-to-pad contact can comprise a minimal total surface area, which can minimize heat transfer between the reader module and the sensor module, making RH measurements more accurate.

In one exemplary embodiment, the center pin 70 can be electrically coupled to an interrupt line 61 of the controller 60, the first pin pair 72 can be electrically coupled to a ground line of the controller, the second pin pair 74 can be electrically coupled to a power line of the controller, the third pin pair 76 can be electrically coupled to a data line of the controller, and the fourth pin pair 78 can be electrically coupled to a clock line of the controller. In this embodiment, the central pad 32 can be electrically coupled to a ground line of the sensor submodule 22, the first ring 34 can be electrically coupled to a power line of the sensor, the second ring 36 can be electrically coupled to a data line of the sensor, and the third ring 38 can be electrically coupled to a clock line of the sensor. In other embodiments, the order of the second, third and fourth pin pairs 74, 76, 78 and the first, second and third rings 34, 36, 38 with the respective controller lines and sensor lines can be rearranged in any manner so long as, when the reader module 50 is inserted into the sleeve 2, the power line of the controller is connected with the power line of the sensor, the data line of the controller is connected with the data line of the sensor, and the clock line of the controller is connected with the clock line of the sensor. In some embodiments, the center pin 70 can be electrically coupled to the ground line of the controller while the first pin pair 72 can be electrically coupled to the interrupt line of the controller.

FIG. 7A shows electrical connections between the components of the reader module 50 and the sensor module 20 in an embodiment where the sensor module 20 comprises at least a sensor submodule 22 and a memory submodule 23. As shown in FIG. 7A, the reader module 50 may comprise a display 64 and/or a transceiver 65, which may be used to output data to a user (e.g., via the display) or wirelessly to a connected device (e.g., to a user's smartphone or some other computing device via the transceiver). The display and/or transceiver may be connected to and controlled by a controller 60 of the reader module 50. The controller 60 further connects to the pin pairs of the connector pins 66, which match up to landing pads 30 of the sensor module 20.

The landing pads 30 can be concentric and symmetric about a center axis extending perpendicular to the coplanar upper surfaces of the landing pads. This symmetry can allow for an electrically equivalent connection to be formed between the connector pins 66 and the landing pads 30 when the reader module 50 is inserted into the sleeve 2, regardless of the rotational orientation, with respect the center axis, of the reader module relative to the sensor module. At any rotational orientation, the pins 66 of the reader module 50 land on the same landing pad 30 and make the same electrical connections. In other words, the electrical connection between the reader module 50 and the sensor module 20 can be rotation non-specific. Because of this rotation non-specific feature, when a user inserts the reader module 50 into the sleeve 2, the user can ignore the rotational orientation of the reader module, making the connection simpler, faster and less prone to connection errors. Because the connection can be made faster, a subsequent RH measurement can be made sooner, leaving less time for heat to transfer between the reader module and the sensor module, and rendering the RH measurement more accurate.

It should be understood that in alternative embodiments, the connector pins 66 can be swapped with the landing pads 30. For example, in some embodiments, the reader module 50 can comprise plural landing pads at a lower end thereof and the sensor module 20 can comprise a set of connector pins at an upper surface that are configured to mate with the landing pads when the reader module is inserted into the sleeve 2. This "reversed" arrangement can be functionally equivalent to the illustrated arrangement.

Figure 7B:
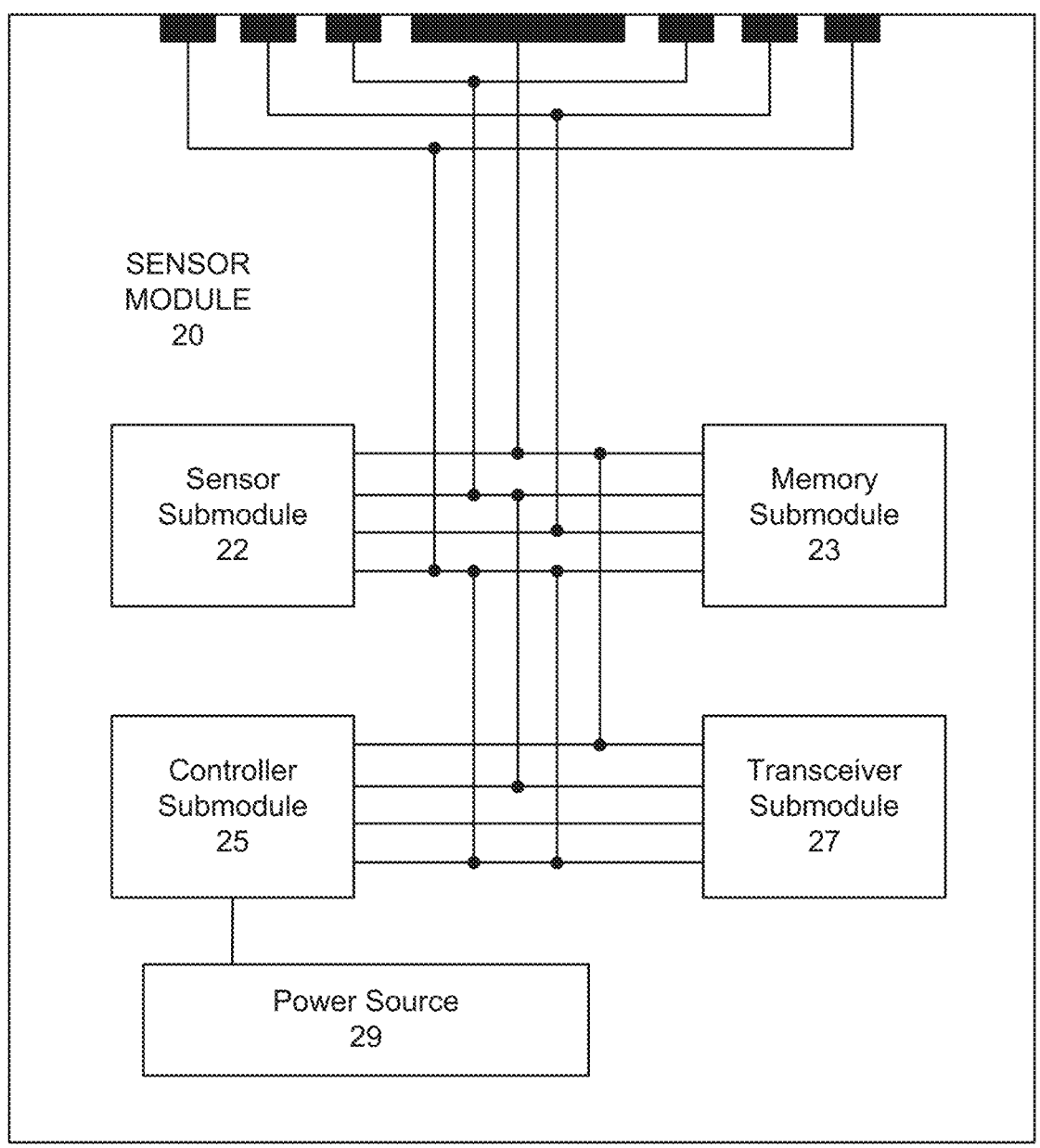
FIG. 7B shows another exemplary sensor module comprising additional components.

The sensor module 20 may comprise at least a sensor submodule 22 and a memory submodule 23, as illustrated in FIG. 7A. Additionally, in some embodiments, the sensor module 20 may also include a controller submodule 25, a power source 29, and/or a transceiver submodule 27, as illustrated in FIG. 7B. The various submodules may be connected to common data/power lines, such as a power line, a clock line, a data line, and a ground line, thus providing a common bus for communication (e.g., using an I2C communication format). In other embodiments (not illustrated), the various subcomponents may be connected in other configurations that rely on other types of communication formats and/or that do not use a common bus.

In some embodiments, the sensor submodule 22 can be an SHT12-HWR-01 Humidity and Temperature Sensor from Sensirion Inc. The sensor can contain a CMOS based single chip multi-sensor providing a digital signal. The sensor can include a capacitive polymer sensing element for relative humidity measurement and a band-gap temperature sensor for temperature measurement. Both can be coupled to a 14-bit analog-to-digital converter and a serial interface circuit on the same chip. The sensor can communicate with the controller via a 2-wire serial interface. In some cases, the controller can download parameter values from the sensor can be used in a conversion formula to determine RH and temperature. The controller can read humidity data and temperature data in digital form from the sensor and use the conversion formula to determine RH and temperature values that can be displayed.

The controller 60 and/or controller submodule 25 can comprise a conventional microcontroller/microprocessor unit that comprises typical hardware, such as an actual processor, memory (e.g., volatile memory and/or non-volatile memory), input/output connectors, etc., as well as embedded firmware and/or software for executing various functionalities.

The memory submodule 23 may be any type of conventional memory unit comprising non-volatile memory (e.g., flash memory) or other memory that is able to store and retrieve data, and may include input/output connectors, as well as embedded firmware and/or software for executing various functionalities.

The transceiver submodule 27 may be a low-power wireless module such as a BLUETOOTH component, a LORAWAN component, or other such wireless transceiver components, and may include input/output connectors, as well as embedded firmware and/or software for executing various functionalities, including routing and networking functionalities.

Having described many structural features of the exemplary embodiments above, the following discussion describes exemplary related functional features and methods of use, with reference to FIGS. 8-12.

The controller 60 can have at least an active mode and a low-power, or standby, mode. In some embodiments, the controller 60 can have additional modes or sub-modes, such as a halt mode. In the active mode, the controller 60 can be configured to interact with the sensor submodule 22 and/or the display to actively read data from the sensor and determine and/or display humidity and temperature values associated with the concrete. In the low-power, or standby, mode, the controller 60 can be configured to passively wait for an interrupt signal, or key change, and then switch to the active mode when the interrupt signal is received.

Figure 8:
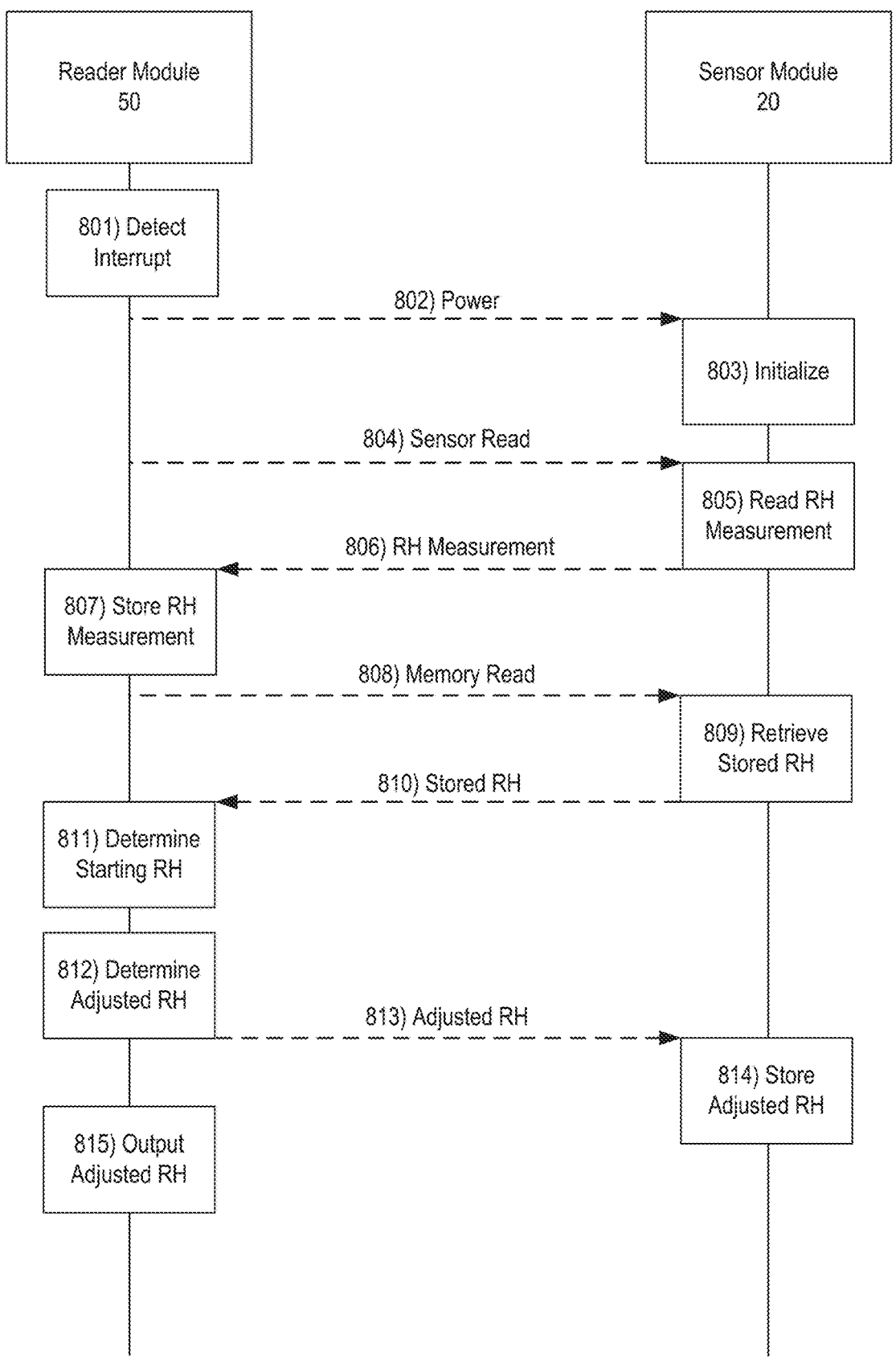
FIGS. 8-10 are flow diagrams showing exemplary methods described herein.

FIG. 8 shows a sequence diagram illustrating an exemplary interaction between a reader module 50 and a sensor module 20 to measure humidity or moisture with sensor drift compensation. The exemplary sequence of FIG. 8 may occur in response to or after a reader module 50 is electrically connected to a sensor module 20.

At step 801, the reader module 50 may begin the sequence of FIG. 8 after detecting an interrupt signal by the controller 60. The interrupt signal may be generated upon connection of the reader module 50 and the sensor module 20. As the reader module 50 and sensor module 20 are brought into contact, the center pin 70 and the first pin pair 72 make contact with the central pad 32, resulting in the center pin 70 becoming electrically coupled to the first pin pair 72, which causes the interrupt signal to the controller 60. The interrupt signal can cause the controller 60 to automatically switch from the low-power mode to the active mode.

The interrupt signal may also be generated when a user selects a "read" option at the reader module 50. For example, the reader module may include a read button (not shown) that generates the interrupt signal in order to start the process of FIG. 8. Additionally, an equivalent signal may be generated in response to an instruction received from another device (e.g., an instruction received from a smartphone or other device connected via the transceiver 65). Additionally, the interrupt signal may be generated every so often (e.g., in response to a time period elapsing, as indicated by a timer (not shown) or a timing process on-board the reader module 50) when the reader module 50 is connected to the sensor module 20.

Thus, the sequence of FIG. 8 may be invoked in several ways so that a reader module 50 may capture one or more drift-adjusted readings from a sensor module 20. For example, the sequence of FIG. 8 may be performed automatically when a reader module 50 is connected to a sensor module 20, which generates an interrupt signal from the connection of the pins 66 to the pads 30, to generate a first drift-adjusted measurement. Continuing the example, after a user selects a read button on the sensor module, or sends a read command from another device (e.g., the user's smartphone), a second drift-adjusted measurement may be generated. Then, a third drift-adjusted measurement may be generated after a time period elapses (e.g., a timer may indicate that 30 minutes have expired since the second drift-adjusted measurement was taken, and cause the interrupt signal to occur). Thus, the sequence of FIG. 8 may be repeated whenever a moisture or humidity measurement is taken.

At step 802, the reader module 50 transmits power to the sensor module 20 (using the power line connection to transmit power from a particular pin to a particular pad) after the interrupt has been detected. Power may be transmitted to each subcomponent of the sensor module 20 using a shared power line (e.g., to a sensor submodule 22, a memory submodule 23, a controller submodule 25, and/or a transceiver submodule 27, as shown at FIGS. 7A-B). The controller 60 may output the power signal to the power line at step 802 a certain time after the interrupt signal is detected (e.g., 0.5 seconds), which may ensure that enough time has elapsed for each of the pins to fully engage the corresponding pads following the initial interrupt signal so that the power signal may be received by the sensor module 20.

At step 803, the sensor module 20 receives power via the power line and enters an active state according to an initialization process. The initialization process may comprise powering up of the subcomponents of the sensor module 20, some of which may have a delay before external signals may be received and processed, code verification and/or self-testing, a subcomponent entering an initial state, and the like. Such initialization procedures may be conducted by each subcomponent in response to receiving a power signal, or, in some embodiments, in response to commands from a controller submodule 25. After initializing at step 803, one or more of the subcomponents of the sensor module 20 may transmit a signal indicating an operating status (e.g., normal operation, error status, etc.) on a data line back to the reader module 50 (not shown in FIG. 8).

The sensor submodule 22 may measure RH during the initialization process and store the RH measurement in memory (e.g., a volatile memory on-board the sensor submodule 22). Additionally or alternatively, the sensor submodule 22 may receive a read signal before capturing an RH measurement.

At step 804, the controller 60 can send a sensor read signal to the sensor submodule 22 of the sensor module 20 to begin reading the sensor. The controller 60 may transmit the sensor read signal to the sensor submodule 22 using a data line, and the sensor read signal may include an address associated with the sensor submodule 22 so that the sensor submodule 22 (as opposed to the memory submodule 23 or some other submodule) receives and responds to the command. The controller 60 may use, for example, the I2C protocol to send the sensor read signal. The controller 60 may initiate step 804 after a certain delay elapses from the time the interrupt signal was received and/or the controller 60 may initiate step 804 in response to receiving a signal from the sensor module 20 indicating that initialization is complete. The time between the interrupt signal and sending the read signal to sensor submodule 22 can be a fraction of a second, minimizing the amount of heat that can be transferred between the reader module 50 and the sensor module 20.

At step 805, the sensor submodule 22 of the sensor module 20 may capture an RH measurement in response to the sensor read signal. The sensor submodule 22 may also or alternatively capture a temperature or some other moisture measurement (e.g., absolute humidity). The captured measurement may be a numeric indication of the relative humidity (e.g., 0.9 to indicate 90%) and/or temperature (e.g., a number indicating degrees), absolute humidity (e.g., in grams per cubic meter), and the like. Additionally or alternatively, the sensor submodule 22 may capture parameters that may be used to calculate some or all of these measurements (e.g., by controller 60 after receipt of the parameters).

In some cases, the sensor submodule 22 may also retrieve one or more RH measurements and/or other measurements from memory (e.g., from a volatile memory on-board the sensor submodule 22), such as an RH measurement taken as part of initialization in step 803. Then, at step 806, the sensor submodule 22 of sensor module 20 may transmit the one or more RH and/or other measurements back to the controller 60 of the reader module 50 (e.g., via a data line). At step 807, the controller 60 of the reader module 50 receives and stores the one or more RH measurements and/or other measurements received from the sensor submodule 22 of the sensor module 20 (e.g., in volatile memory on-board the controller 60). In some cases, the controller 60 may perform calculations on the received RH measurement data to generate a numeric indication of relative humidity, a temperature, an absolute humidity, and the like.

At step 808, the controller 60 sends a memory read signal to a memory submodule 23 of the sensor module 20. The memory read signal may include an address associated with the memory submodule 23. The memory submodule 23 may store past RH and/or other measurements, which may be adjusted for sensor drift. For example, the memory submodule 23 may store drift-adjusted measurements from each previous time the process of FIG. 8 or 9 occurred. Each RH and/or other measurement may be stored along with a timestamp indicating when the measurement was captured.

At step 809, the memory submodule may retrieve any past RH and/or other measurements stored in the memory, along with an associated timestamp for each measurement, and transmit the stored past RH and/or other measurements along with associated timestamps (e.g., on a data line) to the controller 60 of the reader module 50 at step 810. If the memory submodule 23 does not contain any previous measurements, it may transmit an indication that no past measurements are stored.

Based on the past RH and/or other measurements, the drift-adjusted RH measurement may be determined. At step 811, the controller 60 may determine the earliest RH measurement to use for the drift adjustment calculation. The drift adjustment calculation may depend on an amount of time the sensor has been in high RH conditions. Therefore, the controller 60 may determine the earliest RH measurement that shows a sufficiently high RH (e.g., above a certain threshold). This may be referred to as a "starting RH." For example, the earliest RH measurement (based on timestamps) indicating an RH of at least 80% may be considered the starting RH.

In some cases, the controller 60 may choose an RH measurement as the starting RH if each subsequent RH measurement is also sufficiently high (e.g., above a threshold). For example, a first RH measurement may be above a threshold, a second subsequent RH measurement may be below the threshold, and third through nth subsequent RH measurements may be above the threshold. In this situation, the controller 60 may choose the third RH measurement as the starting RH measurement because it is the earliest RH measurement for which all subsequent RH measurements are sufficiently high.

At step 812, the controller 60 of the reader module 50 determines a sensor drift-adjusted RH measurement based on the RH measurement received at step 806 and the stored RH measurements received at step 810. Although any drift-adjustment process could be used, in one embodiment the controller 60 determines an amount to adjust the RH measurement received at step 806 based on an amount of time the sensor submodule 22 has been in high RH conditions. For example, if the timestamp indicates that the starting RH measurement (as determined at step 811) was taken 36 hours prior, the RH measurement received at step 806 may be reduced by a certain amount corresponding to a 36 hour time period. Such an amount may be calculated or determined using various equations or tables that may be specific to a particular sensor, and, in some cases, may take into account other factors such as temperature, absolute humidity, or other factors. A more detailed algorithm for determining a drift-adjusted RH is also described below with respect to FIG. 11.

At step 813, the drift-adjusted RH measurement is sent to the memory submodule 23 of the sensor module 20 along with a timestamp indicating the time it was captured. At step 814, the memory submodule 23 receives and stores the drift-adjusted RH measurement. The memory submodule 23 thus stores the adjusted RH measurement so that it may be used in future sensor drift adjustment calculations (e.g., since it will be retrieved at step 809 in subsequent iterations of the sequence of FIG. 8).

At step 815, the controller 60 of the reader module 50 may cause the drift-adjusted RH measurement to be output to another module or device. In some embodiments, the controller 60 causes display of the adjusted RH measurement on display 64 of the reader module 50. Additionally or alternatively, controller 60 may transmit the adjusted RH measurement (e.g., using transceiver 65) to another device, such as a user's smartphone, a server computer, or the like.

After the sequence of FIG. 8 completes, the reader module 50 may start a timer that, upon expiration, causes another RH measurement to be taken, causes the reader module 50 to enter a low power operation, or the like. The reader module 50 may also, after the sequence of FIG. 8 completes, stop transmitting power to the sensor module 20 in order to conserve power.

Figure 9:
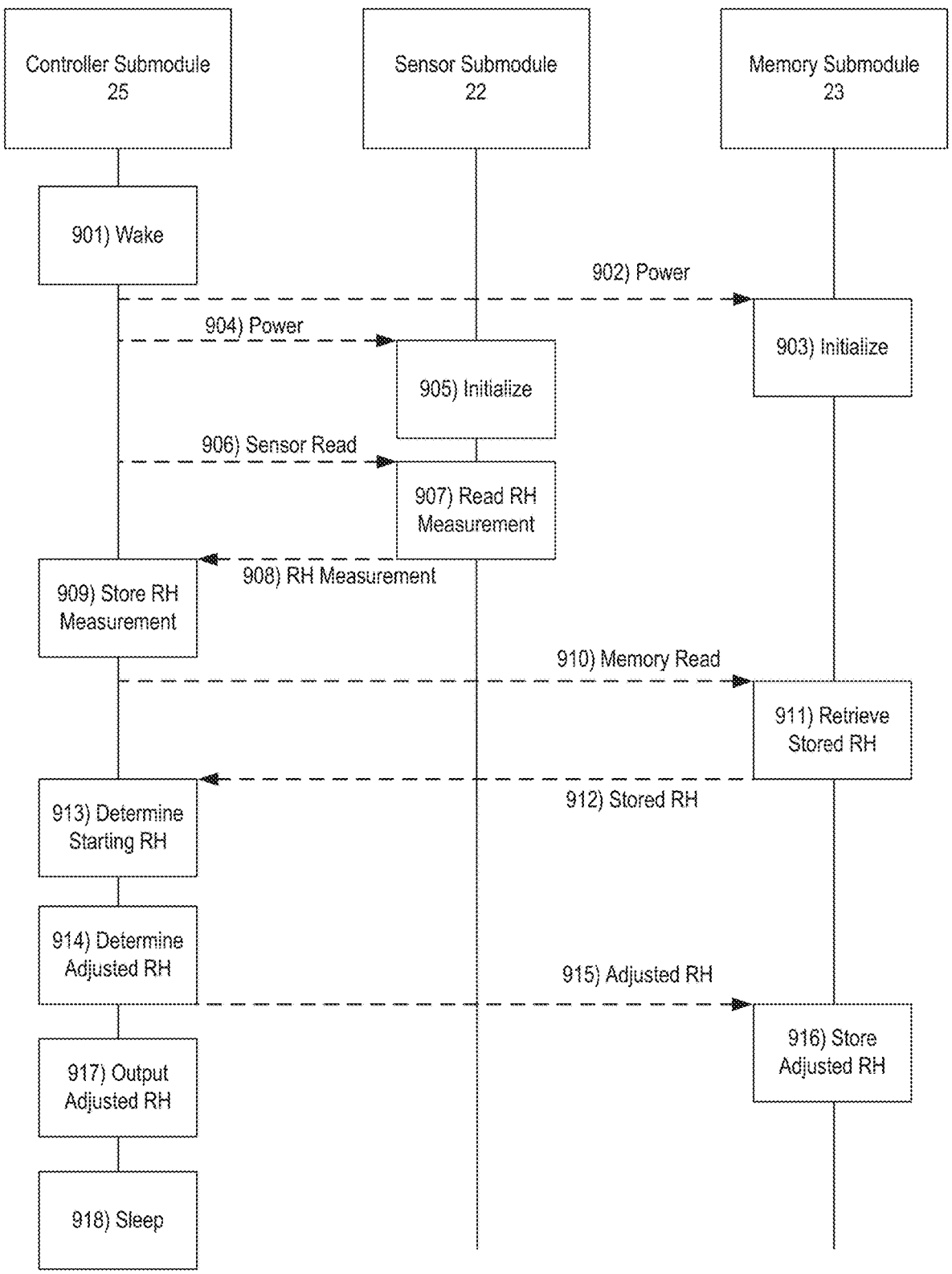

FIG. 9 shows another example sequence that may occur when a sensor module 20 includes an on-board controller submodule 25 and power source 29, as in the embodiment illustrated at FIG. 7B. In these embodiments, the sensor module 20 may wake itself from time to time to capture RH measurements (e.g., at periodic intervals). These embodiments may ensure that RH data is captured more frequently and on a more regular basis for each sensor module 20.

At step 901, the controller submodule 25 may wake itself (e.g., enter an active state from a low power state) based on a timer elapsing. At steps 902 and 904, the controller may output power to subcomponents of the sensor module 20, such as the sensor submodule 22 and the memory submodule 23. If a common power line is used (e.g., as illustrated at FIG. 7B), steps 902 and 904 occur at the same time. Then, at steps 903 and 905 (which occur simultaneously), subcomponents such as sensor submodule 22 and memory submodule 23 may initialize. The initialization process may comprise a delay before external signals may be received and processed by a subcomponent, code verification and/or self-testing, a subcomponent entering an initial state, and the like. Such initialization procedures may be conducted by each subcomponent in response to receiving the power signal, or, in some embodiments, in response to commands from the controller submodule 25. After initializing at step 903 and 905, one or more of the subcomponents of the sensor module 20 may transmit a signal indicating an operating status (e.g., normal operation, error status, etc.) on a data line back to the controller submodule 25.

As discussed above, the sensor submodule 22 may measure RH during the initialization process and store the RH measurement in memory (e.g., a volatile memory on-board the sensor submodule 22). Additionally or alternatively, the sensor submodule 22 may receive a read signal before capturing an RH measurement.

At step 906, similar to step 804 of FIG. 8, the controller submodule 25 can send a sensor read signal to the sensor submodule 22 to begin reading the sensor. The controller submodule 25 may transmit the sensor read signal to the sensor submodule 22 using a data line, and the sensor read signal may include an address associated with the sensor submodule 22 so that the sensor submodule 22 (as opposed to the memory submodule 23 or some other submodule) receives and responds to the command. The controller submodule 25 may use, for example, the I2C protocol to send the sensor read signal. The controller submodule 25 may initiate step 906 after a certain delay elapses from the time the controller submodule 25 woke up and/or the controller submodule 25 may initiate step 906 in response to receiving a signal from the sensor submodule 22 indicating that initialization is complete. The time between wakeup and sending the read signal to sensor submodule 22 can be a fraction of a second.

At step 907, the sensor submodule 22 may capture an RH measurement in response to the sensor read signal. The sensor submodule 22 may also or alternatively capture a temperature or some other moisture measurement (e.g., absolute humidity). The captured measurement may be a numeric indication of the relative humidity (e.g., 0.9 to indicate 90%) and/or temperature (e.g., a number indicating degrees), absolute humidity (e.g., in grams per cubic meter), and the like. Additionally or alternatively, the sensor submodule 22 may capture parameters that may be used to calculate some or all of these measurements (e.g., by controller submodule 25 after receipt of the parameters). In some cases, the sensor submodule 22 may also retrieve one or more RH measurements and/or other measurements from memory (e.g., from a volatile memory on-board the sensor submodule 22), such as an RH measurement taken as part of initialization in step 803. Then, at step 908, the sensor submodule 22 of sensor module 20 may transmit the one or more RH and/or other measurements back to the controller submodule 25 (e.g., via a data line). At step 909, the controller submodule 25 receives and stores the one or more RH measurements and/or other measurements received from the sensor submodule 22 (e.g., in volatile memory on-board the controller submodule 25). In some cases, the controller submodule 25 may perform calculations on the received RH measurement data to generate a numeric indication of relative humidity, a temperature, an absolute humidity, and the like.

At step 910, the controller submodule 25 sends a memory read signal to the memory submodule 23. The memory read signal may include an address associated with the memory submodule 23. The memory submodule 23 may store past RH and/or other measurements, which may be adjusted for sensor drift. For example, the memory submodule 23 may store drift-adjusted measurements from each previous time the process of FIG. 8 or 9 occurred. Each RH and/or other measurement may be stored along with a timestamp indicating when the measurement was captured.

At step 911, the memory submodule 23 may retrieve any past RH and/or other measurements stored in the memory, along with an associated timestamp for each measurement, and transmit the stored past RH and/or other measurements along with associated timestamps (e.g., on a data line) to the controller submodule 25 at step 912. If the memory submodule 23 does not contain any previous measurements, it may transmit an indication that no past measurements are stored.

Based on the past RH and/or other measurements, the drift-adjusted RH measurement may be determined. At step 913, the controller submodule 25 may determine the earliest RH measurement to use for the drift adjustment calculation. The drift adjustment calculation may depend on an amount of time the sensor has been in high RH conditions. Therefore, the controller submodule 25 may determine the earliest RH measurement that shows a sufficiently high RH (e.g., above a certain threshold). This may be referred to as a "starting RH." For example, the earliest RH measurement (based on timestamps) indicating an RH of at least 80% may be considered the starting RH.

In some cases, the controller submodule 25 may choose an RH measurement as the starting RH if each subsequent RH measurement is also sufficiently high (e.g., above a threshold). For example, a first RH measurement may be above a threshold, a second subsequent RH measurement may be below the threshold, and third through nth subsequent RH measurements may be above the threshold. In this situation, the controller submodule 25 may choose the third RH measurement as the starting RH measurement because it is the earliest RH measurement for which all subsequent RH measurements are sufficiently high.

At step 914, the controller submodule 25 determines a sensor drift-adjusted RH measurement based on the RH measurement received at step 908 and the stored RH measurements received at step 912. Although any drift-adjustment process could be used, in one embodiment the controller submodule 25 determines an amount to adjust the RH measurement received at step 908 based on an amount of time the sensor submodule 22 has been in high RH conditions. For example, if the timestamp indicates that the starting RH measurement (as determined at step 913) was taken 36 hours prior, the RH measurement received at step 908 may be reduced by a certain amount corresponding to a 36 hour time period. Such an amount may be calculated or determined using various equations or tables that may be specific to a particular sensor, and, in some cases, may take into account other factors such as temperature, absolute humidity, or other factors. A more detailed algorithm for determining a drift-adjusted RH is also described below with respect to FIG. 11.

At step 915, the drift-adjusted RH measurement is sent to the memory submodule 23 of along with a timestamp indicating the time it was captured. At step 916, the memory submodule 23 receives and stores the drift-adjusted RH measurement. The memory submodule 23 thus stores the adjusted RH measurement so that it may be used in future sensor drift adjustment calculations (e.g., since it will be retrieved at step 911 in subsequent iterations of the sequence of FIG. 9).

At step 917, the controller submodule 25 may cause the drift-adjusted RH measurement to be output to a connected device in embodiments where the sensor module 20 includes a transceiver submodule 27. For example, the controller submodule may establish, via the transceiver submodule 27, a connection to a computing device such as a server device, another nearby sensor device (e.g., in mesh network configurations), or some other computing device, and transfer the drift-adjusted RH measurement for collection, display, or analysis at the computing device. If the sensor module 20 does not include a transceiver submodule 27, step 917 may be skipped.

At step 918, the controller submodule 25 may set a sleep timer that, after elapsing, may cause the controller submodule 25 to wake again to repeat the sequence of FIG. 9, and then it may enter a low power mode.

The sequences of FIGS. 8 and 9 may be used together by a single sensor module 20. For example, the sequence of FIG. 8 may occur whenever a reader module 50 is brought into connection with the sensor module 20. In between such connections, the sensor module 20 may continue to wake up every so often to record drift-adjusted RH readings. Both the adjusted RH measurements determined using the sequence of FIG. 8 and the adjusted RH measurements determined using the sequence of FIG. 9 may be stored in the memory submodule 23, and all of the adjusted RH measurements may be used for determining an adjusted RH measurement according to the sequences of FIG. 8 and FIG. 9.

Figure 10:
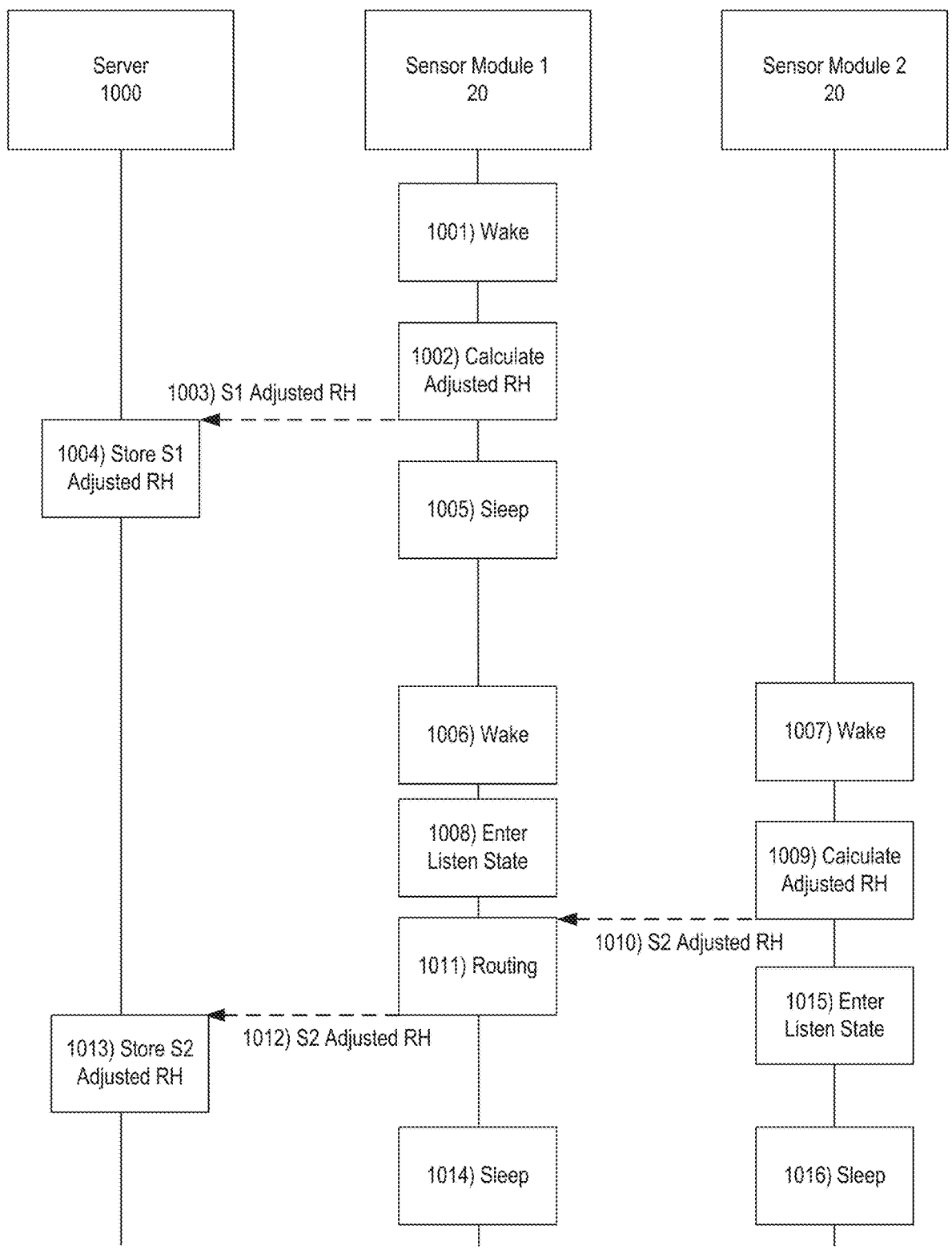

FIG. 10 is an example sequence that illustrates the operation of a network of sensor modules 20 connected to a server 1000. In such a network, the sensor modules 20 can communicate with each other or with the server 1000 directly, depending on factors such as distance between each sensor module 20 and the server 1000, line of sight or other issues affecting reception, battery power, and the like. The network may be a mesh network or another type of network configuration.

At step 1001, a first sensor module 20 may wake in order to take an RH measurement. This may occur as described for step 901 above. At step 1002, the drift-adjusted RH measurement may be calculated. This may occur as described for steps 902-916 above. In other words, to calculate the adjusted RH measurement for step 1002, a controller submodule 25 of the first sensor module 20 may send power to other subcomponent causing them to initialize (e.g., as described for steps 902-904), send a sensor read signal to a sensor submodule 22 of the first sensor module 20 and, in response, receive and store an RH measurement (as described for steps 906-909), send a memory signal to a memory submodule 23 of the first sensor module 20 and, in response, receive stored RH measurements (as described for steps 910-912), determine a starting RH measurement (as described for step 913), determine an adjusted RH measurement (as described for step 914), and transmit and store the adjusted RH measurement in the memory submodule 23 (as described for steps 915-916).

Then, at step 1003, the first sensor module 20 may transmit the adjusted RH measurement to the server 1000 (e.g., using a transceiver submodule 27), which may be in communicable range of the first sensor module 20 so that a direct connection is possible. The transmission may also include a timestamp, a sensor module identifier, and the like. The server 1000 may store the received adjusted RH measurement along with the timestamp, the sensor 1 identifier, and the like at step 1004.

Then, at step 1005, the first sensor module 20 may set a sleep timer and enter a low power mode. A sequence as described for steps 1001-1005 may occur at regular intervals.

At step 1006, the sensor module 20 may wake and enter an active state (e.g., because the sleep timer expired). Simultaneously or at approximately the same time, a second sensor module 20 may also wake (e.g., because a sleep timer of the second sensor module 20 expired) at step 1007. The sensor modules 20 may have set sleep timers so that they wake simultaneously or at approximately the same time so that the sensor modules 20 may communicate with each other for networking purposes. For example, some or all of the sensor modules 20 may wake at regular intervals. At each interval, some or all of the sensor modules 20 may take RH measurements and/or providing networking functions to transmit RH measurements via the network of sensor devices (e.g., via a mesh network to the server 1000).

The first sensor module 20 may enter a listen state after waking at step 1008. For example, if the sensor module 20 has recently taken an RH measurement and/or sent an RH measurement to the server, it may still wake at after a particular interval in order to perform networking functions to transfer data to and/or from other sensor modules 20 and/or other computing devices such as server 1000. In the listening state, a transceiver of the sensor module (e.g., transceiver submodule 27) may be in an active state so that transmissions from other devices may be received. Accordingly, during or before step 1008, a controller submodule 25 may supply power and cause the transceiver submodule 27 to enter an active state.

At step 1009, the second sensor module 20, after waking, may determine a drift-adjusted RH measurement, as described above for step 1002. The second sensor module may then, at step 1010, transfer the drift-adjusted RH measurement to the first sensor module 20 (for example, if the second sensor module 20 detects, using mesh networking protocols, that the first sensor module 20 was in range of, or in communication with other devices in range of, the server 1000). Each sensor module 20 thus may contain networking functionality that uses mesh networking or other networking protocols and standards to determine routing of transmissions. The transmission may also include a timestamp, a sensor module identifier, and the like.

At step 1011, after the transmission from the second sensor module 20 is received at the first sensor module 20, a controller and/or transceiver of the first sensor module 20 may perform routing functionality before forwarding the transmission. For example, the first sensor module 20 may determine a source and destination of the received transmission (e.g., using address information in the transmission), may determine an available route to the destination, an optimal route to the destination, and the like. In the illustrated example, the first sensor module 20 may be in direct communication with the server 1000, which may be the destination for the transmission, so the first sensor module 20 may send the drift-adjusted RH measurement from the second sensor module 20 to the server 1000 at step 1012. The server 1000 may store the received adjusted RH measurement along with the timestamp, the sensor 2 identifier, and the like at step 1013.

At steps 1015, the second sensor module may also enter a listen state so that any transmissions from other devices may be received. In some cases, In the illustrated example sequence, no transmissions from other devices are received. At steps 1014 and 1016, the first and second sensor module 20 enter a sleep state until a later interval, at which time additional RH measurements may be taken and various transmissions may be routed.

The sequence of FIG. 10 merely provides illustrative examples of various ways that multiple sensor modules 20 could communicate in a networked environment. The server 1000 could also send transmissions to various sensor modules directly or indirectly (e.g., via other sensor modules 20). In some cases, a server 1000 or other computing device could have greater transmission range than a sensor module 20 due to a better power source. Thus, the server 1000 could transmit a measurement command directly to a particular sensor module 20 during a listening period (e.g., after the sensor module 20 activates a listen state), and the sensor module 20 could, in response, transmit the requested drift-adjusted RH measurement using one or more transmission hops from sensor module to sensor module. Additionally, in some cases, the server 1000 or some other computing devices could broadcast regular beacons that are received by some or all sensor modules 20 for the purpose of synchronizing timing, setting listening periods, and/or the like.

Figure 11:
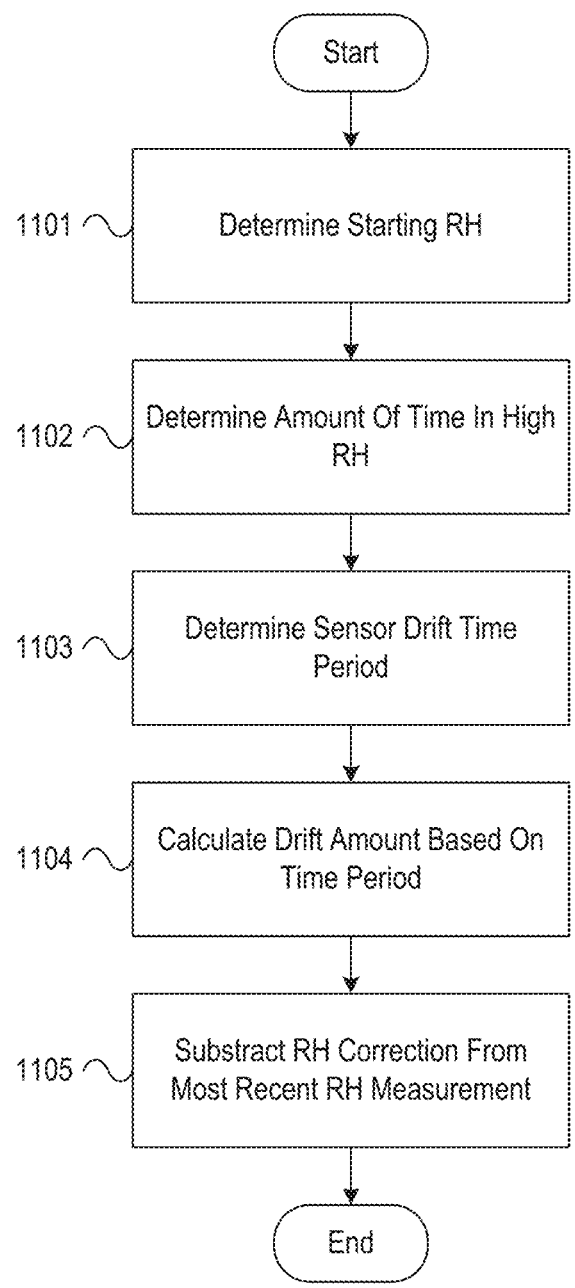
FIG. 11 shows an exemplary algorithm that can be employed by embodiments described herein.

The process of FIG. 11 illustrates an exemplary method for calculating a drift-adjusted RH measurement. Although the illustrated process is one example method for calculating a drift adjusted RH measurement, others could be used with embodiments of the systems and devices described herein.

At step 1101, a controller may determine a starting RH from a sequence of RH measurements associated with timestamps. For example, a controller 60 of a reader module 50 may determine a starting RH as described for step 811, a controller submodule 25 of a sensor module 20 may determine the starting RH as described for step 913, or some other controller may determine a starting RH from a sequence of RH measurements.

The controller thus may determine the earliest RH measurement to use for the drift adjustment calculation. The drift adjustment calculation may depend on an amount of time the sensor has been in high RH conditions. Therefore, the controller may determine the earliest RH measurement that shows a sufficiently high RH (e.g., above a certain threshold). This may be referred to as a "starting RH." For example, the earliest RH measurement (based on timestamps) indicating an RH of at least 80% may be considered the starting RH.

In some cases, the controller may choose an RH measurement as the starting RH if each subsequent RH measurement is also sufficiently high (e.g., above a threshold). For example, a first RH measurement may be above a threshold, a second subsequent RH measurement may be below the threshold, and third through nth subsequent RH measurements may be above the threshold. In this situation, the controller may choose the third RH measurement as the starting RH measurement because it is the earliest RH measurement for which all subsequent RH measurements are sufficiently high.

At step 1102, the controller may determine an amount of time that an RH sensor has been in high relative humidity based on the timestamp associated with the starting RH measurement. The controller thus may subtract, from the present time (or from a time indicated by a timestamp associated with the most recent RH measurement), a time indicated by the timestamp associated with the starting RH. The controller thus determines the amount of time that has elapsed from the starting RH measurement to the present time (or the time of the most recent RH measurement).

Figure 12:
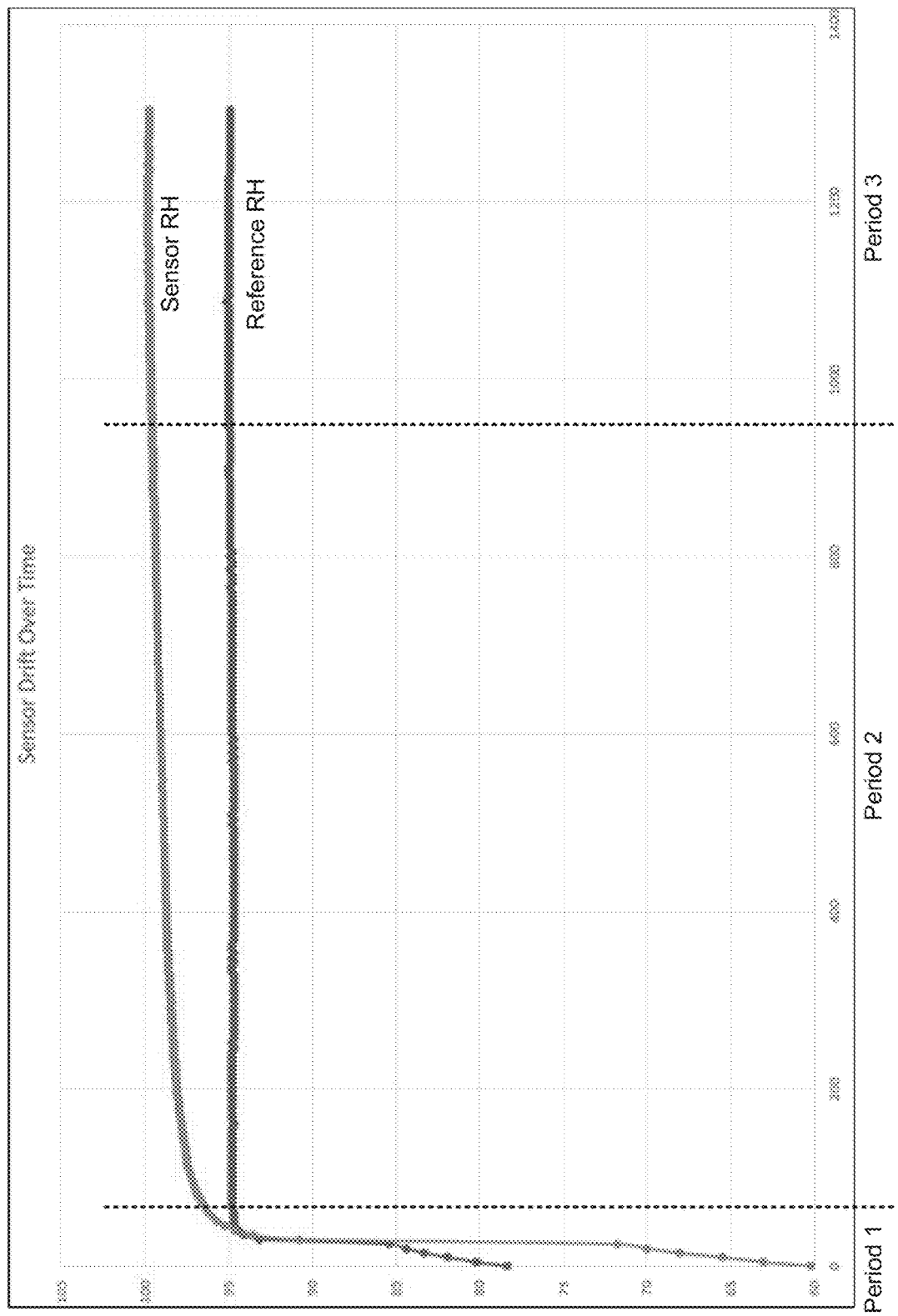
FIG. 12 shows a data plot illustrating an example sensor drift over time.

At step 1103, based on the elapsed time in high RH conditions, the controller may determine a time period. The time period may tend to correspond to a characteristic of a sensor drift curve that describes the sensor drift over time for a particular sensor. For example, as shown at FIG. 12, a sensor reading (shown as Sensor RH) may, during an initial period, require some time to synchronize with an actual RH (shown as Reference RH), and also may not drift very much since little time has elapsed. Thus, during a first time period, no drift adjustment, or only minimal drift adjustment, may be used. During a second period, a sensor drift may increase fairly constantly, and thus, during a second period, a drift amount may need to be adjusted based on the particular time with the second time period. During a third time period, the drift amount may asymptotically approach a maximum drift, and thus the drift may not vary much after entering the third period. Thus, by determining the time period based on the elapsed time, the controller may determine what type of drift adjustment to apply, if any.

The controller may store constants indicating a length of time for the first time period and a length of time for the second time period. The elapsed time determined in step 1102 may be compared to these values to determine the corresponding time period. The length of time for the first period and the length of time for the second time period may vary based on sensor type, sensor manufacturer, temperature, absolute humidity, and other conditions, so a memory of the controller, or a connected memory, may store tables that may be used to look up the appropriate period 1 and period 2 lengths based on the applicable factors. Thus, the controller may perform a table lookup to complete step 1103.

At step 1104, the controller may estimate a drift amount based on the time period determined in step 1103. For the first time period, zero, or a small number, may be used as the drift amount. For the second time period, an equation may be used to estimate the drift amount based on the elapsed time within the second period. Thus, if the elapsed time corresponds to a time within an earlier part of the second time period, the estimated drift amount may be smaller than one that corresponds to a time within a later part of the second time period. The parameters of the equation may specify a maximum drift and a function (e.g., a linear function, a quadratic function, or the like) that increases in correlation with elapsed time. For the third time period, a maximum drift may be used. The maximum drift and/or the equation may also vary based on factors such as sensor type, sensor manufacturer, temperature, absolute humidity, and other conditions, so a table (e.g., the same table discussed for step 1103 or a different table) may be used to lookup the maximum drift amount and/or the equation in order to complete step 1104.

Finally, at step 1105, the controller may subtract the estimated drift amount determined at step 1104 from the most recent RH reading in order to calculate the drift-adjusted RH measurement. For a first time period, the drift-adjusted RH measurement may be the same as the actual RH measurement (i.e., if a drift of zero is used for time period 1).

One or more processes described herein may be embodied in computer-usable data and/or computer-executable instructions, such as in one or more program modules, executed by one or more computing devices. Generally, program modules include routines, programs, objects, components, data structures, etc. that perform particular tasks or implement particular abstract data types when executed by a controller in a computer or other data processing device. The computer executable instructions may be stored on one or more computer readable media such as a hard disk, optical disk, removable storage media, solid-state memory, RAM, etc. The functionality of the program modules may be combined or distributed as desired. In addition, the functionality may be embodied in firmware or hardware equivalents such as integrated circuits, field programmable gate arrays (FPGA), application-specific integrated circuits (ASIC), and the like. Particular data structures may be used to more effectively implement one or more examples of the disclosure, and such data structures are contemplated within the scope of computer executable instructions and computer-usable data described herein.

Aspects of the disclosure have been described in terms of various examples. While examples of systems and methods are shown, it will be understood by those skilled in the art, that the disclosure is not limited to these examples. Modifications may be made by those skilled in the art, particularly in light of the foregoing teachings. For example, each of the features of the aforementioned examples may be utilized alone or in combination or sub-combination. For example, any of the above described systems and methods or parts thereof may be combined with the other methods and systems or parts thereof described above. For example, the steps shown in the figures may be performed in other than the recited order, and one or more steps shown may be optional. It will also be appreciated and understood that modifications may be made without departing from the true spirit and scope of the present disclosure. The description is thus to be regarded as providing examples of, instead of a restriction on, the present disclosure.

What is claimed is:

1. A method comprising:
   receiving, by a reader module, from a sensor of a sensor module installed in a concrete slab, information indicating a first relative humidity;
   receiving, by the reader module, from a memory of the sensor module, information comprising one more previously-recorded indications of relative humidity;
   determining, based on the information indicating the first relative humidity and based on the information comprising one or more previously-recorded indications of relative humidity, an adjusted relative humidity,
      wherein the determining of the adjusted relative humidity comprises determining, based on the information comprising one or more previously-recorded indications of relative humidity, an amount of time that the sensor module has been above a threshold relative humidity level; and
   transmitting, by the reader module, the adjusted relative humidity.

2. The method of claim 1, wherein the determining of the amount of time comprises:
   determining, from the information comprising one or more previously-recorded indications of relative humidity, a particular indication of relative humidity above the threshold relative humidity level; and
   comparing a first timestamp associated with the particular indication of relative humidity to a second timestamp associated with the information indicating the first relative humidity to determine the amount of time.

3. The method of claim 1, wherein the determining of the adjusted relative humidity further comprises determining, based on the amount of time that the sensor module has been above the threshold relative humidity level, a drift adjustment period, wherein the adjusted relative humidity is determined based on the drift adjustment period.

4. The method of claim 3, wherein the determining of the adjusted relative humidity comprises:
   selecting a formula based on the drift adjustment period;
   calculating, using the formula, a drift adjustment; and
   subtracting the drift adjustment from the first relative humidity to determine the adjusted relative humidity.

5. An apparatus comprising:
a relative humidity sensor;
an interface configured to receive a signal that, after being received, causes the sensor to measure information indicating a first relative humidity;
a memory configured to store information comprising one or more previously-recorded indications of relative humidity; and
a controller configured to determine, based on the information indicating the first relative humidity and based on the information comprising one or more previously-recorded indications of relative humidity, an adjusted relative humidity,
wherein the controller is configured to determine the adjusted relative humidity by determining, based on the information comprising one or more previously-recorded indications of relative humidity, an amount of time that the sensor has been above a threshold relative humidity level.

6. The apparatus of claim 5, wherein the controller is configured to determine the amount of time by:
determining, from the information comprising one or more previously-recorded indications of relative humidity, a particular indication of relative humidity above the threshold relative humidity level; and
comparing a timestamp associated with the particular indication of relative humidity to a timestamp associated with the information indicating the first relative humidity to determine the amount of time.

7. The apparatus of claim 5, wherein the controller is configured to determine the adjusted relative humidity by determining, based on the amount of time that the sensor module has been above the threshold relative humidity level, a drift adjustment period, wherein the adjusted relative humidity is determined based on the drift adjustment period.

8. The apparatus of claim 7, wherein the controller is configured to determine the adjusted relative humidity by:
selecting a formula based on the drift adjustment period;
calculating, using the formula, a drift adjustment; and
subtracting the drift adjustment from the first relative humidity to determine the adjusted relative humidity.

9. The apparatus of claim 5, further comprising a transceiver for transmitting the adjusted relative humidity.

10. The apparatus of claim 9, wherein the controller is further configured to:
receive, via the transceiver, another adjusted relative humidity determined by a second apparatus; and
route the another adjusted relative humidity determined by the second apparatus to another computing device.

11. A system comprising:
a sensor module comprising a memory and a sensor; and
a computing device comprising a controller configured to:
after establishing a connection with the sensor module, cause the sensor to determine information indicating a first relative humidity;
receive, from the memory of the sensor module, information comprising one more previously-recorded indications of relative humidity;
determine, based on the information indicating the first relative humidity and based on the information comprising one or more previously-recorded indications of relative humidity, an adjusted relative humidity,
wherein the controller is configured to determine the adjusted relative humidity by determining, based on the information comprising one or more previously-recorded indications of relative humidity, an amount of time that the sensor module has been above a threshold relative humidity level.

12. The system of claim 11, wherein the connection is established by physically connecting pin pairs of the computing device with landing pads of the sensor module.

13. The system of claim 11, wherein the controller is configured to determine the amount of time by:
determining, from the information comprising one or more previously-recorded indications of relative humidity, a particular indication of relative humidity above the threshold relative humidity level; and
comparing a timestamp associated with the particular indication of relative humidity to a timestamp associated with the information indicating the first relative humidity to determine the amount of time.

14. The system of claim 11, wherein the controller is configured to determine the adjusted relative humidity by determining, based on the amount of time that the sensor module has been above the threshold relative humidity level, a drift adjustment period, wherein the adjusted relative humidity is determined based on the drift adjustment period.

15. The system of claim 14, wherein the controller is configured to determine the adjusted relative humidity by:
selecting a formula based on the drift adjustment period;
calculating, using the formula, a drift adjustment; and
subtracting the drift adjustment from the first relative humidity to determine the adjusted relative humidity.

16. The system of claim 11, wherein the sensor module further comprises a wireless transceiver for establishing the connection, wherein the sensor module is further configured to:
receive, via the wireless transceiver, another adjusted relative humidity determined by a second sensor module; and
route the another adjusted relative humidity determined by the second sensor module to the computing device.

* * * * *